(12) United States Patent
Ratner

(10) Patent No.: US 8,402,964 B2
(45) Date of Patent: *Mar. 26, 2013

(54) NEONATAL COLORIMETRIC CARBON DIOXIDE DETECTOR

(75) Inventor: Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/566,123

(22) Filed: Aug. 3, 2012

(65) Prior Publication Data

US 2012/0296229 A1    Nov. 22, 2012

Related U.S. Application Data

(63) Continuation of application No. 12/472,011, filed on May 26, 2009, now Pat. No. 8,256,414.

(51) Int. Cl.
*A61M 11/00* (2006.01)
*A61M 15/00* (2006.01)
*A61M 16/00* (2006.01)
*A62B 5/08* (2006.01)
*A62B 9/00* (2006.01)
*A62B 18/00* (2006.01)

(52) U.S. Cl. ......... 128/200.23; 128/200.24; 128/205.23; 128/207.17; 422/86; 600/532

(58) Field of Classification Search ............ 128/200.23, 128/200.24, 205.23, 207.17; 422/86
See application file for complete search history.

(56) References Cited

U.S. PATENT DOCUMENTS

| | | | | |
|---|---|---|---|---|
| 4,205,043 A * | 5/1980 | Esch et al. | ................... | 422/416 |
| 4,211,239 A * | 7/1980 | Raemer et al. | ................. | 600/529 |
| 4,879,999 A * | 11/1989 | Leiman et al. | ........... | 128/207.14 |
| 5,005,572 A * | 4/1991 | Raemer et al. | ........... | 128/207.14 |
| 5,197,464 A * | 3/1993 | Babb et al. | ............... | 128/207.14 |
| 5,273,029 A * | 12/1993 | Wilk et al. | ............... | 128/200.26 |
| 5,291,879 A * | 3/1994 | Babb et al. | ............... | 128/200.26 |
| 5,375,592 A * | 12/1994 | Kirk et al. | ................. | 128/207.14 |
| 5,468,451 A * | 11/1995 | Gedeon | .......................... | 422/416 |
| 5,765,550 A * | 6/1998 | Psaros et al. | ............ | 128/202.27 |
| 5,846,836 A * | 12/1998 | Mallow | ......................... | 436/169 |
| 5,965,061 A * | 10/1999 | Larsson et al. | ............. | 252/408.1 |
| 6,144,869 A * | 11/2000 | Berner et al. | ................ | 600/347 |
| 6,187,596 B1 * | 2/2001 | Dallas et al. | .................. | 436/169 |
| 6,378,522 B1 * | 4/2002 | Pagan | ....................... | 128/207.14 |
| 6,502,573 B1 * | 1/2003 | Ratner | ...................... | 128/207.17 |
| 8,256,919 B2 * | 9/2012 | Ratner | ...................... | 128/200.24 |
| 2010/0310425 A1 * | 12/2010 | Piper | .............................. | 422/86 |

OTHER PUBLICATIONS

Aziz et al., The pediatric disposable end-tidal carbon dioxide detector role in endotracheal Intubation in newborns. J. of Perinatology 19(2): 110 (1999).*
Cardoso et al., Portable devices used to detect endotracheal intubation during emergency situations: a review. Critical Care Medicine 26(5): 957 (1998).*
Garey et al., Tidal volume threshold for colorimetric carbon dioxide detectors available for use in neonates. Pediatrics 121 : e1524 (Jun. 2008).*
Garey et al., Tidal volume threshold for colorimetric carbon dioxide detectors available for use in neonates. Pediatrics 121: e1524 (Jun. 2008).

* cited by examiner

*Primary Examiner* — Ethan C Whisenant
(74) *Attorney, Agent, or Firm* — Larson & Larson, P.A.; Frank Liebenow; Justin Miller

(57) ABSTRACT

A neonatal colorimetric carbon dioxide detector has a colorimetric carbon dioxide detector membrane having a pH-sensitive chemical indicator that undergoes colorimetric change in the presence of carbon dioxide. The detector has a patient orifice in fluid communication with the baby's airway and a respiration equipment orifice connected to a breathing system. The patient orifice is connected to a breathing tube and when the breathing tube is inserted correctly into the trachea, as the baby exhales, carbon dioxide interacts with the colorimetric membrane which changes color based upon the concentration of carbon dioxide. The internal volume of the neonatal colorimetric carbon dioxide detector is reduced to properly function with low-birth-weight (neonatal) infants.

19 Claims, 4 Drawing Sheets

NEONATAL COLORIMETRIC CARBON DIOXIDE DETECTOR

CROSS-REFERENCE TO RELATED APPLICATION

This application is a continuation of U.S. patent application Ser. No. 12/472,011, filed May 26, 2009, the disclosure of which is hereby incorporated by reference.

FIELD OF THE INVENTION

The present invention relates in general to the field of colorimetric carbon dioxide detectors, particularly for use with low-birth weight neonatal patients.

BACKGROUND

Airway adapters are generally used with patients being given respiratory assistance, such as patients under anesthesia, or patients on life support systems, to connect between the patient airway (mouth, nose, tracheal tube) and a ventilating tube of a breathing apparatus. The ventilating tubes convey breathing gases to the patient and exhaled breath away from the patient (typically, the airway adapter is in the form of a short connector of tubular shape making a connection between the generally different cross sections of tubes).

End-tidal carbon dioxide ($ETCO_2$) detection provides a non-invasive indication of the proper insertion of the airway tube is obtained by the analysis of the exhaled breath gases. End-tidal carbon dioxide ($ETCO_2$) detection indicates to the clinician whether the airway tube is inserted correctly into the trachea. If inserted correctly, carbon dioxide is detected. If the airway tube is inserted incorrectly (into the esophagus), no carbon dioxide is detected and the clinician knows to remove the airway tube and reinsert it.

Airway components are typically made as plastic injection moldings, keeping production costs low. The amount of void volume (also known as dead space) in such airway components is typically very considerable. For neonatal applications, especially those with low birth weight, the patient has very little exhalation air volume. Airway adapters needs to have minimal added void volume to reduce the effects of gas mixing which would adversely affect the integrity of a colorimetric carbon dioxide detector membrane. Existing devices claim to have 3 mL of internal volume (dead space), when in actuality, these devices have 5 mL of internal volume before they are inserted into a circuit and 3 mL of internal volume after inserted into a circuit.

There exists a serious need for a sampling airway adapter for use with low birth weight neonatal patients, which overcomes the disadvantages of available adapters by reducing the internal volume when inserted into a circuit and used with neonatal patients.

SUMMARY OF THE INVENTION

A neonatal colorimetric carbon dioxide detector has a colorimetric carbon dioxide detector membrane having a pH-sensitive chemical indicator that undergoes colorimetric change in the presence of carbon dioxide. The detector has a patient orifice in fluid communication with the baby's airway and a respiration equipment orifice connected to a breathing system. The patient orifice is connected to a breathing tube and when the breathing tube is inserted correctly into the trachea, as the baby exhales, carbon dioxide interacts with the colorimetric membrane which changes color based upon the concentration of carbon dioxide. In some embodiments, the total internal volume of the neonatal colorimetric carbon dioxide detector is less than or equal to 3.8 mL before being attached to a breathing circuit and the neonatal colorimetric carbon dioxide detector adds less than or equal to 1 mL to a breathing circuit after being inserted.

In one embodiment, a neonatal colorimetric carbon dioxide detector is disclosed including an enclosure having a patient orifice in fluid communication with a patient's airway and a respiration equipment orifice, the respiration equipment orifice is partially occluded thereby reducing an internal volume of the respiration equipment orifice. The respiration equipment orifice is also in fluid communication with the patient orifice and the patient orifice overlaps and is offset with respect to the respiration equipment orifice. A colorimetric membrane is held within the enclosure and visible from outside of the enclosure. The colorimetric membrane is situated such that exhalation gas from the patient orifice passes around and/or through the colorimetric membrane before leaving the respiration equipment orifice.

In another embodiment, a neonatal colorimetric carbon dioxide detector is disclosed including a patient orifice in fluid communication with a patient's airway and a respiration equipment orifice in fluid communication with the respiration equipment orifice. The respiration equipment orifice is partially occluded thereby reducing an internal volume of the respiration equipment orifice. A bottom surface of the respiration equipment orifice overlaps and is offset with respect to a top surface of the patient orifice. A colorimetric membrane is held between the respiration equipment orifice and the patient orifice. The colorimetric membrane is in fluid communication with the patient orifice such that exhalation gas from the patient orifice passes through and around the colorimetric membrane before leaving out of the respiration equipment orifice. For neonatal application in patients of low birth weight, it is preferred, though not required, that the total internal volume of the respiration equipment orifice and the patient orifice is less than or equal to 3.8 mL before being attached to a breathing circuit and the neonatal colorimetric carbon dioxide detector adds less than or equal to 1 mL to a breathing circuit after being inserted.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
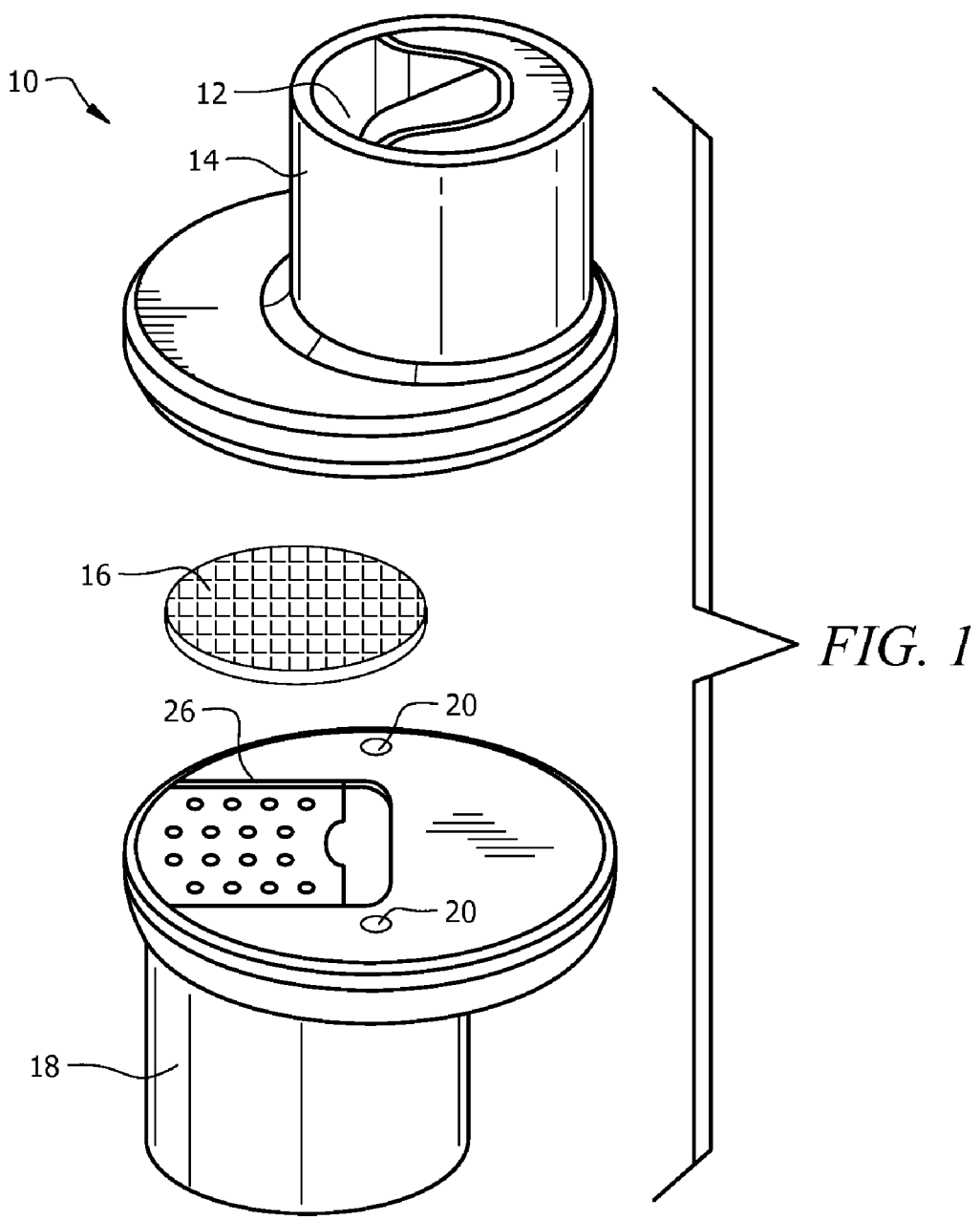
FIG. 1 illustrates a perspective view of a neonatal colorimetric carbon dioxide detector of the present invention.

Reference will now be made in detail to the presently preferred embodiments of the invention, examples of which are illustrated in the accompanying drawings. Throughout the following detailed description, the same reference numerals refer to the same elements in all figures.

The present invention discloses a neonatal colorimetric carbon dioxide detector 10 suited for low birth weight neonatal patients (low birth weight babies are often classified as those who weigh less than 2.5 kg).

Figure 2:
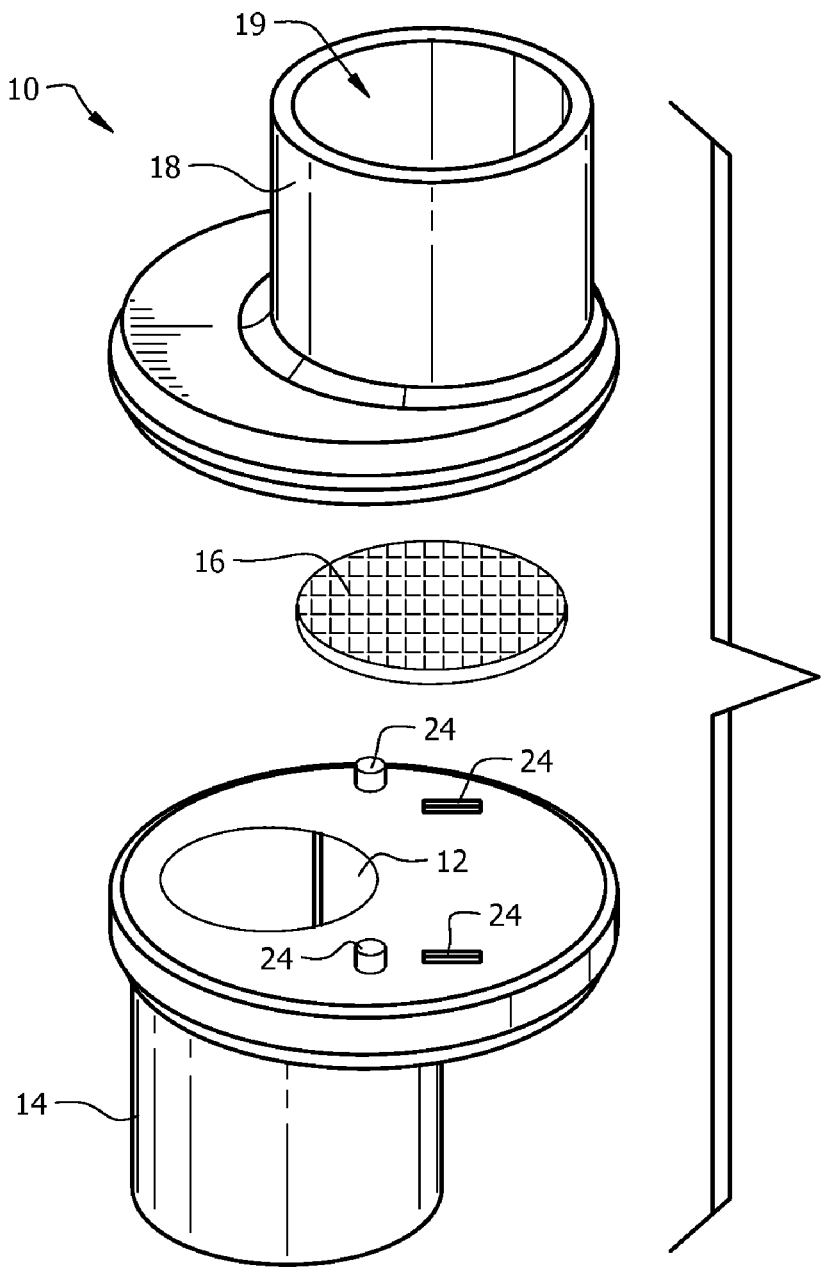
FIG. 2 illustrates a second perspective view of a neonatal colorimetric carbon dioxide detector of the present invention.

Referring to FIGS. 1 and 2, top and bottom perspective views of a neonatal colorimetric carbon dioxide detector 10 of the present invention are shown. Although one specific method of fabrication and construction of the neonatal colorimetric carbon dioxide detector 10 is shown, many such methods and fabrication techniques are known and all are anticipated an included here within.

Figure 5:
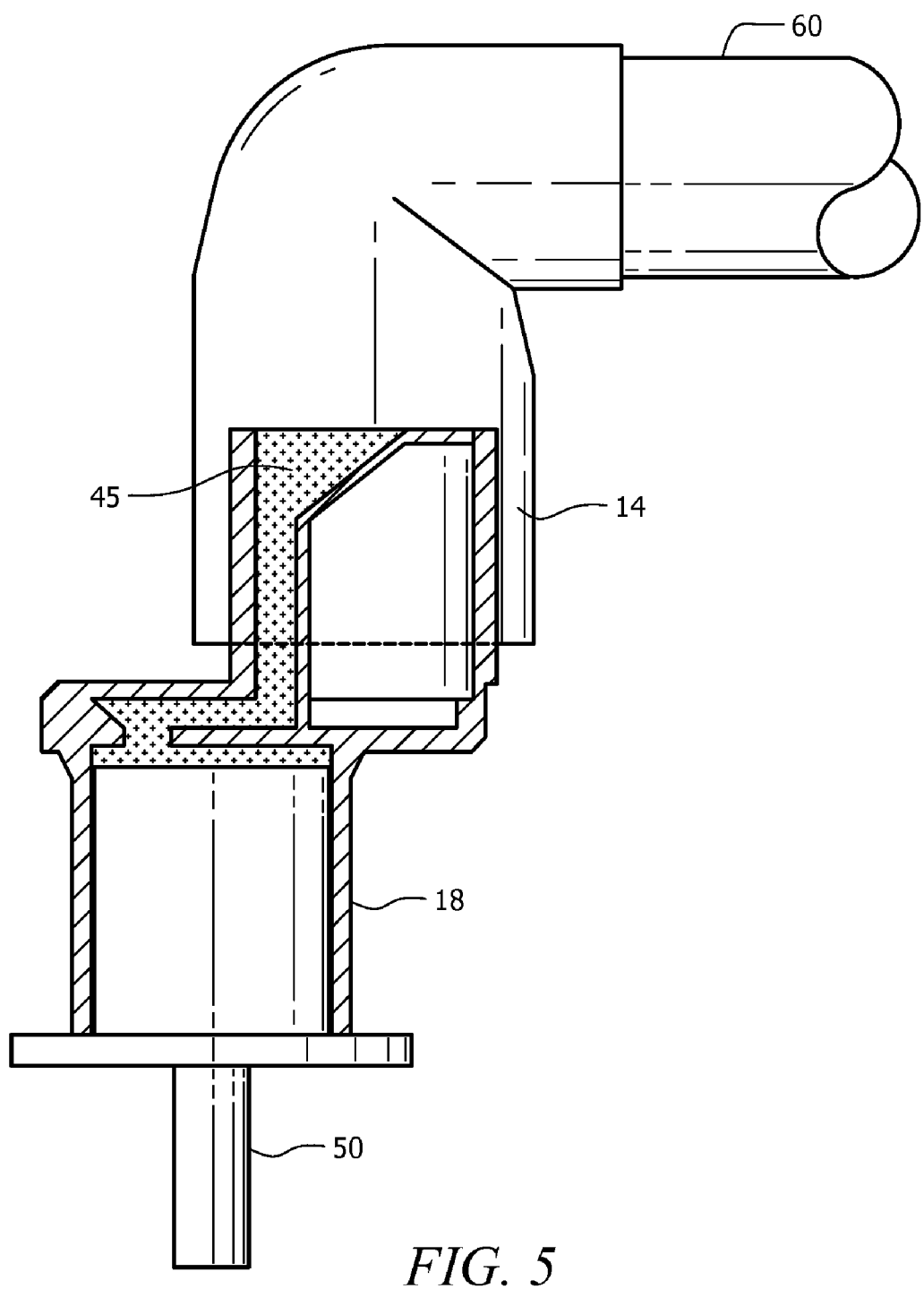
FIG. 5 illustrates a cross-sectional view of the neonatal colorimetric carbon dioxide detector of the present invention.

The example of FIGS. 1 and 2 includes a top molded section 14, a bottom molded section 18 and a colorimetric membrane 16. The top molded section 14 includes a respiration equipment orifice 12 for accepting air flow from a breathing device (e.g., a breathing bag or ventilation equipment, not shown). In many examples of the prior art, the respiration equipment orifice 12 is open and hollow, thereby providing an area for expired gases to be held. As shown in FIGS. 1 and 5, the respiration equipment orifice 12 is partially occluded, thereby reducing the internal volume of the neonatal colorimetric carbon dioxide detector 10.

The bottom molded section 18 includes a patient orifice 19 for communicating with the patient. The top molded section 14 and the bottom molded section 18 form an enclosure 10 having a respiration equipment orifice 12 at the top and a patient orifice 19 at the opposite end.

The colorimetric membrane 16 is held on one side above a perforated grill section 26 and kept in place by, for example, two molded protrusions 24 on the inside surface of the top molded section 14. Although one specific method of fabrication and holding of the colorimetric membrane 16 in position while marrying the top molded section 14 to the bottom molded section 18 is shown, many such methods and fabrication techniques are known and all are anticipated an included here within. The colorimetric membrane 16 is situated in fluid communication with the air flow from the patient orifice 19 such that, as the patient exhales, the colorimetric membrane 16 is exposed to the exhaled gases as the exhaled gases pass around and/or through the colorimetric membrane 16. Therefore, the colorimetric membrane 16 will change color depending upon the presence and the concentration of the gas of interest (e.g., carbon dioxide). For example, one typical carbon dioxide colorimetric membrane 16 is blue when no $CO_2$ is present, green when 1% to 2% $CO_2$ is present, yellow/green when 2% to 5% $CO_2$ is present and yellow when more than 5% $CO_2$ is present. In another example, another typical carbon dioxide colorimetric membrane 16 is purple when less than 0.5% $CO_2$ is present, tan when 0.5% to 2% $CO_2$ is present, mustard yellow when 2% to 5% $CO_2$ is present and yellow when more than 5% $CO_2$ is present. To prevent exposure to the gas of interest before use, it is known to ship the neonatal colorimetric carbon dioxide detector 10 in a hermetically sealed container or bag.

There are many ways known to join the top molded section 14 and the bottom molded section 18, one of which is to have one or more pegs, posts or snaps 24 that fit into holes 20. The neonatal colorimetric carbon dioxide detector 10 is preferably made from a transparent or translucent material, making the colorimetric membrane 16 is visible from outside through a surface of the neonatal colorimetric carbon dioxide detector 10.

Figure 3:
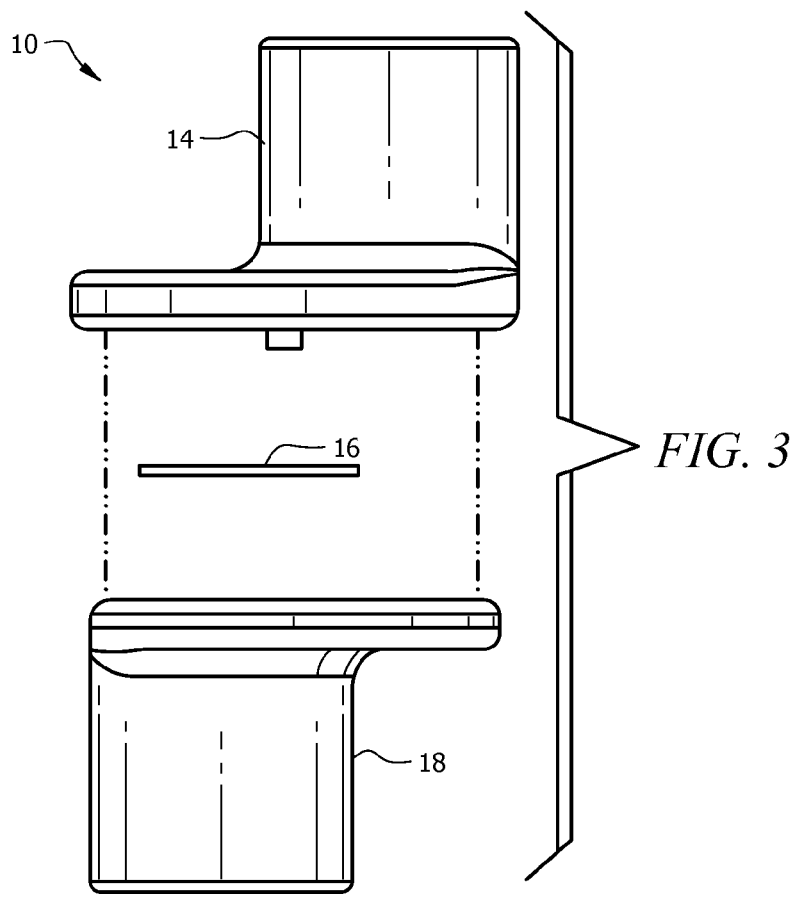
FIG. 3 illustrates a plan view of the neonatal colorimetric carbon dioxide detector of the present invention before assembly.

Referring to FIG. 3, a plan view of the neonatal colorimetric carbon dioxide detector 10 is shown before assembly. Shown, is the relationship of the top molded section 14 and the bottom molded section 18 with the colorimetric membrane 16 positioned to be held between the top molded section 14 and the bottom molded section 18. There are many ways known to join the top molded section 14 and the bottom molded section 18, one of which is to have one or more pegs, posts or snaps 24 that fit into holes 20, thereby holding the top molded section 14 and the bottom molded section 18 together with or without an adhesive. Other methods include the use of adhesives, ultrasonic welding, etc.

Figure 4:
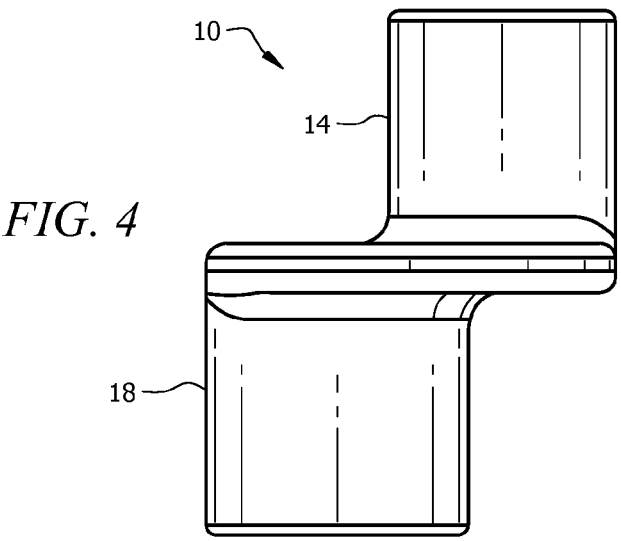
FIG. 4 illustrates a plan view of the neonatal colorimetric carbon dioxide detector of the present invention after assembly.

Referring to FIG. 4, a plan view of the present invention after assembly is shown. Once the top molded section 14 and the bottom molded section 18 of the neonatal colorimetric carbon dioxide detector 10 are assembled around the colorimetric membrane 16, the total internal air volume is approximately 3.8 mL or less than 3.8 mL. Insertion of the neonatal colorimetric carbon dioxide detector 10 into an airway circuit increases the total internal air volume 45 (see FIG. 5) by approximately 1 mL and preferably by less than 1 mL.

As is shown in FIG. 4, the top molded section 14 overlaps and is offset from the bottom molded section 18. This arrangement provides for a relative short distance between the respiration equipment orifice 12 within the top molded section 14 and the patient orifice 19 within the bottom molded section 18. The offset satisfies the need for visual inspection of the colorimetric membrane 16, while keeping internal volume to a minimum.

Referring to FIG. 5, a cross-sectional view of the present invention after assembly is shown. The neonatal colorimetric carbon dioxide detector top molded section 14 interfaces to respiration equipment through, for example, a gas tube 60. The bottom molded section 18 interfaces to the patient through, for example, a tracheal or endo-tracheal tube 50. The total internal air volume is approximately 3.8 mL or less than 3.8 mL. Insertion of the neonatal colorimetric carbon dioxide detector 10 into an airway circuit increases the total internal air volume 45 by approximately 1 mL and preferably by less than 1 mL.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A neonatal colorimetric carbon dioxide detector, the neonatal colorimetric carbon dioxide detector formed to insert into an airway circuit, the neonatal colorimetric carbon dioxide detector comprising:

an enclosure having a patient orifice in fluid communication with a patient's airway and a respiration equipment orifice, the respiration equipment orifice in fluid communication with the patient orifice, the respiration equipment orifice being partially occluded thereby reducing an internal volume of the respiration equipment orifice, the patient orifice overlaps and is offset with respect to the respiration equipment orifice; and a colorimetric membrane held within the enclosure and visible from outside of the enclosure, the colorimetric membrane in fluid communication with the patient orifice such that the colorimetric membrane is exposed to exhalation gas from the patient orifice before the exhalation gas exits through the respiration equipment orifice.

2. The neonatal colorimetric carbon dioxide detector of claim 1, wherein the colorimetric membrane changes color in response to exposure to carbon dioxide gas.

3. The neonatal colorimetric carbon dioxide detector of claim 1, wherein the total internal volume of the enclosure is approximately 3.8 mL and insertion of the neonatal colorimetric carbon dioxide detector into the airway circuit increases the total internal volume of the airway circuit by approximately 1 mL.

4. The neonatal colorimetric carbon dioxide detector of claim 2, wherein the colorimetric membrane changes color from blue to green in response to exposure to exhalation gas having 1% to 2% of carbon dioxide gas.

5. The neonatal colorimetric carbon dioxide detector of claim 2, wherein the colorimetric membrane changes color to yellow/green in response to exposure to exhalation gas having 2% to 5% of carbon dioxide gas.

6. The neonatal colorimetric carbon dioxide detector of claim 2, wherein the colorimetric membrane changes color to yellow in response to exposure to exhalation gas having greater than 5% of carbon dioxide gas.

7. A neonatal colorimetric carbon dioxide detector with carbon dioxide detection, the neonatal colorimetric carbon dioxide detector formed to insert into an airway circuit, the neonatal colorimetric carbon dioxide detector comprising:
    an enclosure having a patient orifice in communication with a patient's airway and a respiration equipment orifice, the respiration equipment orifice in fluid communication with the patient orifice, the respiration equipment orifice connected to the patient orifice by two pegs on a bottom surface of the respiration equipment orifice mating with two holes on a top surface of the patient orifice, the respiration equipment orifice is partially occluded thereby reducing an internal volume of the respiration equipment orifice, the patient orifice overlaps and is offset with respect to the respiration equipment orifice; and
    a colorimetric membrane held within the enclosure and visible through the enclosure, the colorimetric membrane in fluid communication with the patient orifice such that the colorimetric membrane is exposed to exhalation gas from the patient orifice before the exhalation gas exits through the respiration equipment orifice.

8. The neonatal colorimetric carbon dioxide detector of claim 7, wherein the colorimetric membrane changes color in response to exposure to carbon dioxide gas.

9. The neonatal colorimetric carbon dioxide detector of claim 8, wherein the colorimetric membrane changes color from blue to green in response to exposure to exhalation gas having 1% to 2% of carbon dioxide gas.

10. The neonatal colorimetric carbon dioxide detector of claim 8, wherein the colorimetric membrane changes color to yellow/green in response to exposure to exhalation gas having 2% to 5% of carbon dioxide gas.

11. The neonatal colorimetric carbon dioxide detector of claim 8, wherein the colorimetric membrane changes color to yellow in response to exposure to exhalation gas having greater than 5% of carbon dioxide gas.

12. The neonatal colorimetric carbon dioxide detector of claim 7, whereas a total internal volume of the enclosure is approximately 3.8 mL before the neonatal colorimetric carbon dioxide detector is inserted into the airway circuit and the neonatal colorimetric carbon dioxide detector adds less than or equal to approximately 1 mL to the airway circuit after the neonatal colorimetric carbon dioxide detector is inserted into the airway circuit.

13. A neonatal colorimetric carbon dioxide detector with carbon dioxide detection, the neonatal colorimetric carbon dioxide detector formed to insert into an airway circuit, the neonatal colorimetric carbon dioxide detector comprising:
    a patient orifice in fluid communication with a patient's airway;
    a respiration equipment orifice in fluid communication with the patient orifice, a bottom circumferential edge of the respiration equipment orifice interfaced to and overlapping a top circumferential edge of the patient orifice, the patient orifice overlaps and is offset with respect to the respiration equipment orifice; and
    a colorimetric membrane held between the respiration equipment orifice and the patient orifice, the colorimetric membrane is visible through the respiration equipment orifice, the colorimetric membrane in fluid communication with the patient orifice such that the colorimetric membrane is exposed to exhalation gas from the patient orifice before the exhalation gas exits through the respiration equipment orifice, the respiration equipment orifice being partially occluded thereby reducing an internal volume of the respiration equipment orifice.

14. The neonatal colorimetric carbon dioxide detector of claim 13, wherein the colorimetric membrane changes color in response to exposure to carbon dioxide gas.

15. The neonatal colorimetric carbon dioxide detector of claim 14, wherein the colorimetric membrane changes color from blue to green in response to exposure to exhalation gas having 1% to 2% of carbon dioxide gas.

16. The neonatal colorimetric carbon dioxide detector of claim 14, wherein the colorimetric membrane changes color to yellow/green in response to exposure to exhalation gas having 2% to 5% of carbon dioxide gas.

17. The neonatal colorimetric carbon dioxide detector of claim 14, wherein the colorimetric membrane changes color to yellow in response to exposure to exhalation gas having greater than 5% of carbon dioxide gas.

18. The neonatal colorimetric carbon dioxide detector of claim 13, whereas a total internal volume of the respiration equipment orifice and the patient orifice is less than or equal to approximately 3.8 mL before the neonatal colorimetric carbon dioxide detector is inserted into the airway circuit and the neonatal colorimetric carbon dioxide detector adds less than or equal to approximately 1 mL after the neonatal colorimetric carbon dioxide detector is inserted into the airway circuit.

19. The neonatal colorimetric carbon dioxide detector of claim 13, whereas the neonatal colorimetric carbon dioxide detector adds less than or equal to approximately 1 mL after the neonatal colorimetric carbon dioxide detector is inserted into the airway circuit.

* * * * *